United States Patent [19]

Gunterman

[11] 4,261,432
[45] Apr. 14, 1981

[54] AIRLINE EARPHONE STRUCTURE

[76] Inventor: Joseph L. Gunterman, 353 W. Johnson St., Palatine, Ill. 60067

[21] Appl. No.: 31,114

[22] Filed: Apr. 18, 1979

[51] Int. Cl.³ .............................................. A61B 7/02
[52] U.S. Cl. .................................. 181/131; 181/135; 179/1 ST
[58] Field of Search .................. 181/131, 135, 137; 179/1 ST, 156 R, 107 R

[56] References Cited

U.S. PATENT DOCUMENTS

| 999,225 | 8/1911 | Hopewell | 181/137 |
| 2,142,407 | 1/1939 | Norton et al. | 181/135 |
| 2,487,038 | 11/1949 | Baum | 181/135 |
| 2,739,660 | 3/1956 | French | 181/135 |
| 3,080,011 | 3/1963 | Henderson | 181/135 |
| 3,899,044 | 8/1975 | Stumpf et al. | 181/131 |

Primary Examiner—Donald A. Griffin
Assistant Examiner—Benjamin R. Fuller
Attorney, Agent, or Firm—McDougall, Hersh & Scott

[57] ABSTRACT

An acoustically driven earphone for use with entertainment systems in airplanes which transmits acoustical energy from a transducer to the user's ear. The earphones are formed from two resilient plastic tubes each having one end connected to the transducer with each other end connected to the user's ear canal. A wire frame is provided inside the plastic tubes to maintain a preferred configuration.

3 Claims, 7 Drawing Figures

U.S. Patent      Apr. 14, 1981      4,261,432
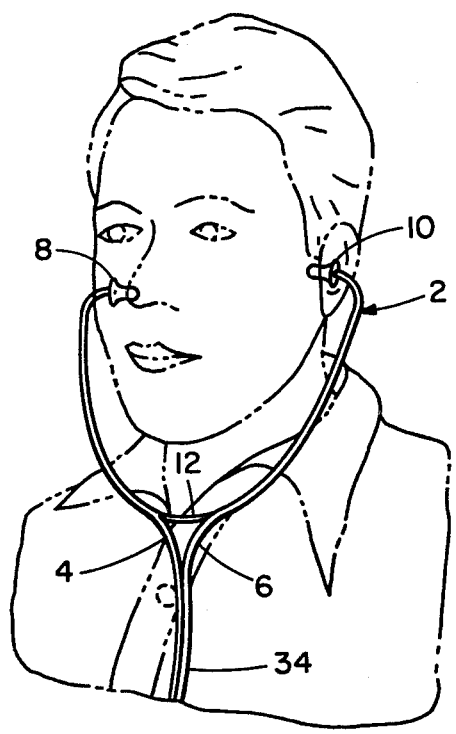
FIG.1
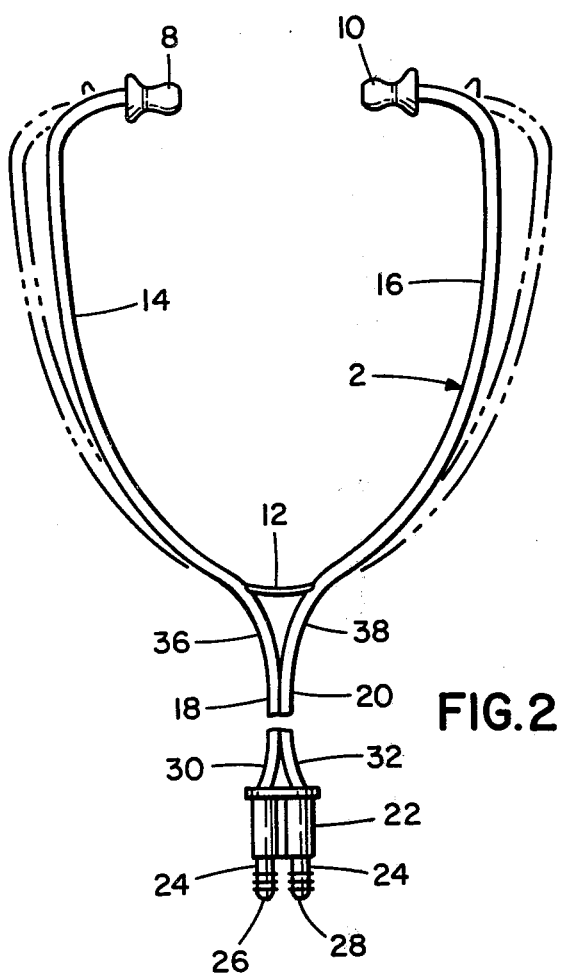
FIG.2
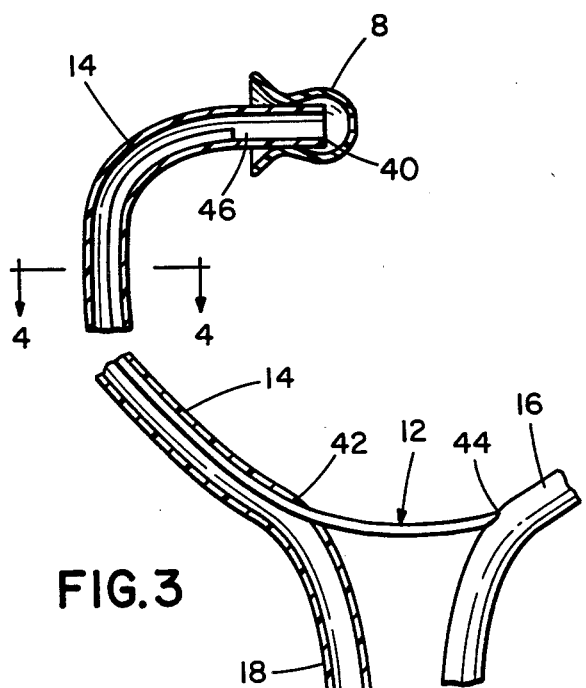
FIG.3
FIG.4
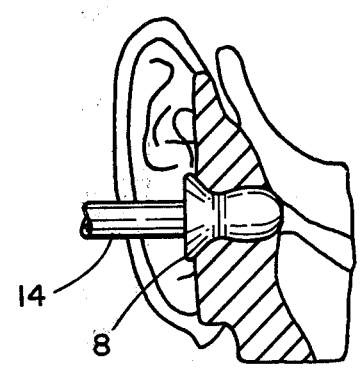
FIG.5
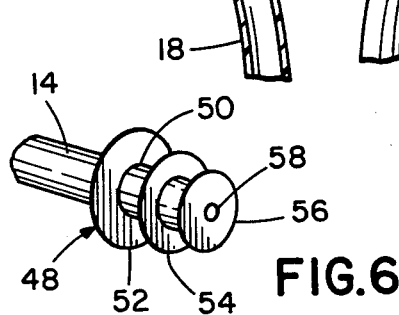
FIG.6
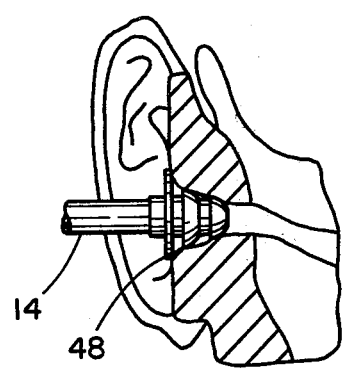
FIG.7

AIRLINE EARPHONE STRUCTURE

BACKGROUND OF THE INVENTION

This invention relates generally to acoustically driven earphones. More specifically it relates to acoustically driven earphones which are used by passengers in commercial aircraft in conjunction with the aircraft entertainment system.

Typically, in such a system, music or a soundtrack of a movie in the form of an electrical signal is fed to each seat in the aircraft. An electrical transducer is provided in the arm of each passenger's seat. The electrical transducer converts the electrical signal to the actual acoustic signal, i.e. the music or the soundtrack. The passenger may listen to the music by using an acoustically driven earphone. The earphone is basically a pair of flexible tubes each having one end connected to the transducer with the other ends disposed in the passenger's ear canals. The earphone is called an acoustically driven device in that it couples the sound waves from a transducer to the ear. These earphones are lightweight and extremely durable since they, themselves, contain no electrical components.

Although the principle involved in acoustically driven earphones, i.e. the transmission of acoustic waves using tubes, is not very complex, the earphone must have certain elements to allow it to function. The main function of the earphone is to couple and transmit acoustic energy from the transducers to the ears. A plug is usually provided by cementing it to the end of the tubes to permit the tubes to removably engage the transducers. Also, ear inserts are provided on the other ends of the tubes so that those ends may be seated in the ear canals. The known art has provided means for constructing the above three elements, i.e., the plug, the tubes, and the ear inserts, out of durable and flexible plastics such as polyvinylchloride or polyethylene. There is, however, one more very important function of the earphone and that is the retention of the ear insert and associated tube within the ear canal.

There are several methods known for retaining the insert within the ear canal. The first is to provide arcuate end portions at the ends of the tubes so that they will extend over the top of the earlobes as shown in U.S. Pat. No. 3,667,569 to Mackey et al. Another method is to provide the insert with annular mushroom shaped flanges which will engage the ear canal, or the ear insert may be moulded to be anchored in the concha of the outer ear. Both of these techniques are shown in U.S. Pat. No. 3,080,011 to Henderson. Lastly, the ear inserts may be attached to a flexible frame so that they are urged toward one another. This is the principle used in the common stethoscope or in U.S. Pat. No. 3,539,032 to Scanlon where it has been adapted for use in airline entertainment systems.

Stethoscope-like devices all work on basically the same principles to retain the ear inserts within the ear canal. The ear inserts are connected to the ends of curved stiff non-resilient tubes; the tubes being joined near their opposite ends by a narrow u-shaped piece of spring metal. Flexible resilient tubes are connected to the ends of the stiff non-resilient tubes and serve to transmit acoustic energy from a source such as a sound transducer.

Thus, in the stethoscope, the stiff curved tubes and spring material co-operate to form a frame to hold the ear inserts in a common plane and also urge the inserts towards each other. A user may put on the stethoscopic earphones by spreading the rigid tubes apart and positioning the ear inserts just outside the ear canals. When the tubes are released, the spring will urge the ear inserts together and seat the inserts in the ear canals, the entire ear phone thus being supported by the ear canal.

The classic stethoscope design described above is constructed of various discrete elements. Rigid tubes must be made of a different material than the flexible tubes. Also, an elongated u-shaped piece of spring metal must be provided and all of the above must be assembled together. There have been some variations on this classic design which have allowed the substitution of less expensive materials requiring a simplified assembly.

One example of such an improvement is disclosed in U.S. Pat. No. 3,539,032 to Scanlon. There, the plastic tubes are heat-set in a curved configuration at the ends where the ear inserts are provided. A small slider member is provided to attach the two heat treated tubes together. Thus, the heat treatment of the tubes change their characteristics of flexibility and resiliency to a more rigid and non-resilient form. Although this does allow a less expensive ear phone to be made, it does rely heavily upon the characteristics of the tubes after heat treatment. If they are stiffened too much, they will break when strained. If they are not heat treated sufficiently, they will not be elastic enough to urge the ear inserts into the ear canal for proper seating.

Another approach to providing a structure which is somewhat less sophisticated is presently in extensive use in the industry. The ear inserts are connected directly to one end of the flexible tubes, the other ends of the flexible tubes are provided with the appropriate plug to allow connection to the transducer. The ear phone is then provided with a plastic channel much in the shape of the frame of the classic stethoscope. The flexible tubes are inserted within the channel so that the external plastic frame will provide the necessary stiffness and elasticity while the flexible tube inside the channel carries the acoustic wave to the ear. This use of the hollow plastic frame is not without drawbacks either. Since the plastic must surround the tube on three sides, the frame is somewhat bulky. Despite the virtues of many synthetic plastic materials available today, they will readily break if sufficiently deformed.

Hence, the stethosopic acoustically driven earphones in the prior art are either fragile, or relatively expensive to manufacture and maintain in proper working order.

It is, therefore, an object of this invention to provide an acoustically driven earphone which can be inexpensively manufactured.

It is further an object of this invention to provide an acoustically driven earphone which is extremely durable in use.

It is an object of this invention to provide an earphone requiring a minimum of maintenance.

It is also an object of this invention to provide an acoustically driven earphone which is strengthened by the use of a piece of wire made of steel, another metal, or similar high strength materials.

It is another object of this invention to provide an acoustically driven earphone in which the stiffening frame is essentially retained within the flexible plastic tubes used to transmit the accoustic energy.

Other objects and advantages of the invention will become apparent from the remaining portion of the specification.

SUMMARY OF THE INVENTION

The invention involves the use of a thin wire frame retained inside the acoustic transmitting tubes of an earphone.

The acoustic earphones are coupled to a transducer by use of a removable plug and transmit the acoustical energy to the user's ears by means of tubes which are coupled to the ear canal by soft ear inserts. The inserts and associated tubes are retained at the user's ears by means of a flexible wire frame, a substantial part of which is located within the acoustic transmission tubes.

BRIEF DESCRIPTION OF THE DRAWINGS

The invention itself is set forth in the claims appended hereto and forming a part of this specification, while an understanding of embodiments thereof may be had by reference to the detailed description taken in conjunction with the drawings in which:

FIG. 1 is a perspective illustration of one embodiment of the invention in use;

FIG. 2 is a fragmented front elevation view of an embodiment of the invention illustrating it in a flexed position by the use of phantom lines;

FIG. 3 is a fragmented view of sections of an embodiment of the invention showing the left portion in cross-section;

FIG. 4 is a view along line 4—4 of FIG. 3;

FIG. 5 is a horizontal cross-sectional view of the ear canal and lobe with the ear insert plug and associated tube in place;

FIG. 6 is a perspective view of an alternate ear insert plug which may be used to practice the invention;

FIG. 7 is a horizontal cross-sectional view of the ear canal and lobe with the alternate ear insert plug of FIG. 6, and associated tubes in place.

DETAILED DESCRIPTION OF THE INVENTION

FIGS. 1 and 2 illustrate an embodiment of the invention as worn by the user. The airline earphone device 2, is comprised of two tubes 4 and 6, each having ear inserts 8 and 10, respectively, stiffening wire 12, and plug 24. The tubes 4 and 6 have upper sections 14 and 16, and lower sections 18 and 20, the latter being as long as necessary to reach the transducer. Plug 22 is used to facilitate connection of the transducer.

Plug 22 is provided with annular seals 24 formed on projections 26 and 28 to engage the connection of the transducer. The ends 30 and 32 of tubes 4 and 6 are cemented to the plug. Tubes 4 and 6 are joined together at their adjacent edges as can be best seen in FIG. 1 in the area marked 34. As they extend to the re-enforcing wire 12, they branch into the separate sections 36 and 38. The separated tubes eventually terminate at the ear insert as can best be seen in FIG. 3 at point 40.

The most salient portion of the invention, however, is the use of stiffening wire 12 which may be constructed of aluminum, iron, steel, or the like. The wire is inserted into the upper sections 14 and 16 of the tubes by penetrating their walls thereby creating openings 42 and 44. The wire itself forms the stiffening frame for the upper portions of the tubes. Referring to FIG. 4, it can be seen that the outer diameter of stiffening wire 12, should be only a fraction of the inner diameter of the tube 14, so as not to significantly reduce the area available inside the tubes for the transmission of acoustic energy.

The stiffening wire terminates at point 46 just before reaching the area of the ear insert 8. This is for two reasons. Since the stiffening wire is terminated before the end 40 of the tube, the tube and ear insert are allowed a good deal of freedom to flex in any direction. This enhances the ability of the ear insert to seat comfortably within the ear canal. Therefore, although FIG. 5 shows the ear insert and ear canal at a position perpendicular to the side of the face, some individuals may have ear canals which are slightly skewed. Thus the more flexible design can be well suited to their needs. Secondly, if the thin stiffening wire were allowed to protrude to the end of the tube, it could present a safety hazard to the user. A violent dislodgement of the earphone could cause the wire end to penetrate the surrounding tube or ear insert and scrape the skin or ear canal of the user. Since the end of the wire is remotely located from the end of the tube where the earphone contacts the user's ear, that possibility is eliminated.

FIG. 6 illustrates an alternate form of ear insert 48, which may be used to practice this invention. The shank 50 is provided with annular skirt-like projections 52, 54 and 56, which are graduated in size. Hole 58 communicates to the end of the upper section 14 of the tube. FIG. 7 shows the alternative ear insert in position within the ear canal. As can be seen from that illustration, the annular skirt-like projections flex to engage the inner surface of the ear canal.

The greatest advantage of the use of the wire is achieved by selecting the most suitable metal. A mild steel or soft iron wire provides an ideal combination of plasticity, elasticity, and durability.

The plasticity of the wire is utilised to allow users of the earphone to adjust the spacing of the ear inserts. Since there is a wide variation between head sizes from children to young adults to adults, it is desirable for the user to reform the frame so that it takes on the appropriate shape most comfortable for extended use. Without this property, the earphone would be too loose on a small head and too tight on a larger head. Actually, the frame should be adjusted so the spacing of the ear inserts is slightly less than it will be when the ear inserts are seated in the ear canal. This is so that the elasticity of the frame may be properly utilised.

The elasticity of the frame is taken advantage of in two ways. First, in order to put the headphone on, the user must grasp the sides of the frames and elastically stretch the frame to a position as shown in the phantom lines of FIG. 2. This is so that the ear inserts can be passed over the outer structure of the ear and positioned at the entrance to the ear canal. The user should then release the sides of the frame so that the elastic forces will urge the inserts into the ear canal. Synthetic plastics generally have less of an ability to undergo a large amount of strain without reaching their plastic limit.

Secondly, the elastic properties of the wire frame are taken advantage of to urge the ear inserts against the ear canal; this being a major function of the earphone. The spacing between the inserts when the frame is unstrained is less than when the inserts are seated in the ear canal. The resulting elastic forces urge the inserts towards each other and the entire earphone is retained in place.

The exceptional durability of the wire frame is of great importance when the earphone is used in the tight quarters of an airplane. Often, the earphones must be stowed in small compartments where they are inadvertently bent or twisted in abnormal ways. Also, when the passengers use the earphones, they must adjust them as detailed above. Passengers often store the earphones in crowded seatback pockets where the earphones may be inadvertently mis-shaped. Finally, in a crowded cabin, earphones are often sat upon or stepped on. In view of the above treatment which the earphone often receives, it is imperative that the frame can be bent back into proper shape on many occasions during its lifetime. Of course, the plastic tubes are resilient enough to withstand this and the metal wire is remarkably durable especially when compared to more brittle synthetic plastic frames.

It is contemplated that the invention described may be varied by the substitution of various types of materials and dimensions of elements without departing from the essence of the invention. It is intended by the claims appended hereto to cover all such variations in design and materials as come within their scope.

What is claimed as new and desirable to be secured by Letters Patent is:

1. An improved earphone including a pair of adjacent resilient tubes separated near the head of the user, a pair of acoustic transducers for connecting the adjacent ends of said tubes to a source of acoustic energy, a pair of ear couplers for coupling each separated end of each said tube to an ear canal of the user, the improvement comprising:

a resilient stiffening wire being U-shaped, an opening defined by the wall of each said tube, said tubes having an inner diameter substantially greater than the outer diameter of said wire, each leg being inserted into a tube through one of said openings at points near the beginning of the separation of the tubes, each leg of said wire running the substantial length of the separated tube portion with the end of each leg of said wire terminating at respective points located short of said separated ends and before reaching the ear couplers thereby allowing the tube ends and associated ear couplers to flex, whereby the stiffening wire provides the separated portions of the tubes with a U-shape having adjustable tension and whereby said flex permits the user to comfortably seat the ear coupler in the ear canal by flexing the coupler to a comfortable position, and wherein the U-shaped stiffening wire braces the beginning of separation of the pair of tubes to inhibit further separation of said tubes.

2. The acoustic earphone device of claim 1 wherein said stiffening wire is constructed of a metal selected from a group consisting of aluminum, iron, and steel.

3. The acoustic earphone device of claim 1 wherein said tubes have an outside diameter in the range of 0.1 inches to 0.4 inches.

* * * * *